(12) United States Patent
Kim et al.

(10) Patent No.: US 8,697,020 B2
(45) Date of Patent: Apr. 15, 2014

(54) SILICA MAGNETIC PARTICLES HAVING A SPHERICAL FORM AND A PROCESS FOR PREPARING THE SAME

(75) Inventors: Jae-Ha Kim, Daejeon (KR); Jong-Gwang Park, Daejeon (KR); Jong-Hoon Kim, Daejeon (KR); Han-Oh Park, Daejeon (KR)

(73) Assignee: Bioneer Corporation, Daejeon (KR)

( * ) Notice: Subject to any disclaimer, the term of this patent is extended or adjusted under 35 U.S.C. 154(b) by 797 days.

(21) Appl. No.: 12/867,413

(22) PCT Filed: Feb. 13, 2009

(86) PCT No.: PCT/KR2009/000718
§ 371 (c)(1),
(2), (4) Date: Nov. 15, 2010

(87) PCT Pub. No.: WO2009/102171
PCT Pub. Date: Aug. 20, 2009

(65) Prior Publication Data
US 2011/0054162 A1  Mar. 3, 2011

(30) Foreign Application Priority Data

Feb. 14, 2008 (KR) ............ 10-2008-0013545
Nov. 21, 2008 (KR) ............ 10-2008-0116512

(51) Int. Cl.
*C01B 33/12* (2006.01)
*C01B 33/20* (2006.01)
*C07H 21/02* (2006.01)
*C07H 21/04* (2006.01)

(52) U.S. Cl.
CPC ............ *C01B 33/12* (2013.01); *C01B 33/20* (2013.01); *C07H 21/02* (2013.01); *C07H 21/04* (2013.01)
USPC .......................................... 423/339

(58) Field of Classification Search
None
See application file for complete search history.

(56) References Cited

U.S. PATENT DOCUMENTS

| | | | |
|---|---|---|---|
| 5,520,917 A | 5/1996 | Mizuguchi et al. | |
| 5,523,231 A | 6/1996 | Reeve | |
| 5,665,554 A | 9/1997 | Reeve et al. | |
| 6,027,945 A | 2/2000 | Smith et al. | |
| 6,270,937 B2 * | 8/2001 | Yuasa et al. | 430/108.7 |
| 6,607,667 B2 | 8/2003 | Pryor et al. | |
| 6,673,631 B1 | 1/2004 | Tereba et al. | |
| 7,183,002 B2 | 2/2007 | Sauer et al. | |
| 8,026,328 B2 * | 9/2011 | Rowell | 528/10 |

FOREIGN PATENT DOCUMENTS

| | | |
|---|---|---|
| JP | 06047273 A | 2/1994 |
| JP | 2001136970 A | 5/2001 |
| JP | 3253638 B2 | 2/2002 |
| JP | 2003104996 A | 4/2003 |
| KR | 0541282 B1 | 12/2005 |
| KR | 1020060061494 A | 6/2006 |
| KR | 1020070018501 A | 2/2007 |

OTHER PUBLICATIONS

R. Boom et al., "Rapid and Simple Method for Purification of Nucleic Acids", Journal of Clinical Microbiology, Mar. 1990, p. 495-503, vol. 28, No. 3.

* cited by examiner

*Primary Examiner* — Eric S Olson
(74) *Attorney, Agent, or Firm* — The Webb Law Firm

(57) ABSTRACT

The present invention relates to silica magnetic particles having a spherical form and a process for preparing the same. The silica magnetic particles prepared according to the present invention, which are silica particles that includes the magnetic particles and additionally have the functional group on the surfaces, has an advantage that the particle size distribution is uniform. Further, the silica magnetic particles prepared according to the present invention can be used as a reagent for separating biomaterials and a reagent for detecting biomaterials.

25 Claims, 8 Drawing Sheets

Results

| | Mean (mV) | Area (%) | Width (mV) |
|---|---|---|---|
| Zeta Potential (mV): -39.8 | Peak 1: -39.8 | 100.0 | 4.90 |
| Zeta Deviation (mV): 4.90 | Peak 2: 0.00 | 0.0 | 0.00 |
| Conductivity (mS/cm): 0.0149 | Peak 3: 0.00 | 0.0 | 0.00 |

| Results | | Mean (mV) | Area (%) | Width (mV) |
|---|---|---|---|---|
| Zeta Potential (mV): 20.0 | Peak 1: | 20.0 | 100.0 | 7.18 |
| Zeta Deviation (mV): 7.18 | Peak 2: | 0.00 | 0.0 | 0.00 |
| Conductivity (mS/cm): 0.00974 | Peak 3: | 0.00 | 0.0 | 0.00 |

SILICA MAGNETIC PARTICLES HAVING A SPHERICAL FORM AND A PROCESS FOR PREPARING THE SAME

TECHNICAL FIELD

The present invention relates to silica magnetic particles, a process for preparing the same, and a method for separating biomaterials using the silica magnetic particles.

BACKGROUND ART

In recent years, a study on a material for bio related research and bio medical service using magnetic substances has been frequently attempted. In particular, studies on a material for separating biomaterials and a use as a medical material have been actively attempted. Among others, a study on magnetic functional silane coated particles where organic functional compounds are coated on magnetic particles has been progressed so that the magnetic functional silane coated particles can be used for separation and purification of DNA and RNA, separation and purification of protein and amino acid, a bio sensor, a drug delivery system, magnetic resonance imaging (MRI) contrast agent, local warm-heating treatment, etc.

The magnetic particles start to be frequently applied as basic materials used in biotechnology research and have been used to quickly and simply separate the biomaterials. A method for separating biomaterials, in particular, nucleic acid or protein according to the related art needs much time and labor force since it should perform several extracting and centrifugal separating steps but degrades the yield and purity of the separated biomaterials and is not suitable for use as a method for automation or mass separation. However, in recent research, special magnetic particles were prepared and a method for very quickly and efficiently separating biomaterials using magnetic particles under appropriate buffer conditions was developed (U.S. Pat. No. 5,523,231, and U.S. Pat. No. 5,665,554).

Further, when using the above-mentioned method for separating biomaterials, an automation method, which can simultaneously process many samples and separate the biomaterials, can be provided. For example, when using a robot automatic apparatus, several hundreds or several thousands of samples can be automatically processed and desired biomaterials can be separated from the samples in large quantities.

In order to discriminate nucleic acid or protein from several cell mixtures, an effective and reproducible separating method is needed, and then a separating method using magnetic particles has been recently developed.

The separation of nucleic acid (DNA and RNA) from the biological samples is the most important step in a biochemistry research and diagnostic process.

If genetic materials (nucleic acid) are not separated from the samples, genetic detection, genetic cloning, genetic sequencing, genetic amplification, cDNA synthesis, and the like, which are subsequent steps, can not be performed. A method for separating nucleic acid using magnetic particles is a separating method that induces a bonding with biomaterials using the magnetic particles and then applies external magnetic field to samples, wherein it is known that the proper size of the magnetic particles used for separating and purifying DNA, RNA, protein, etc., is generally approximately 500 to 2000 nm.

As such, in order for the magnetic particles to be used for the separation and purification of gene (nucleic acid) or protein, it is preferable that they should have magnetic properties as well as should be conjugated with a functional group that bonds a gene or a specific protein on the surfaces of the particles. To this end, there is a need to coat the magnetic particles using the organic functional group or silica.

Among the magnetic particles used for separating the above-mentioned biomaterials, iron oxide particles are representative. The magnetic iron oxide particles generally exist as magnetite ($Fe_3O_4$), maghemite ($Fe_2O_3$), or hematite ($Fe_2O_3$) and the magnetic iron oxide particles can be used to separate and purify biomaterials, for example, nucleic acid (DNA and RNA), separate and purify protein, purify peptide and polypeptide, purify lipids, and the like.

The methods for preparing magnetic particles for separating biomaterials according to the related art can prepare the magnetic particles without agglomeration and interaction between the magnetic particles only by preparing magnetic iron or iron oxide particles from iron salt compounds using a liquid-phase reduction method and coating the prepared magnetic iron or iron oxide particles with silica, polymer or gold or silver, which are a non-magnetic materials. In recent years, among these magnetic particles, silica magnetic particles were being mainly developed (U.S. Pat. No. 6,027,945, U.S. Pat. No. 6,673,631, U.S. Pat. No. 7,183,002, and JP Patent No. 3253638). However, the silica magnetic particles has disadvantages in that a preparing process is complicated, the particle form is uneven, the separation yield in the separation and purification of biomaterials such as nucleic acid, and the like is degraded.

Meanwhile, a method for preparing silica magnetic particles having a spherical form from a method that forms a W/O type emulsion using sodium silicates aqueous solution and emulsifier, adds ammonium sulfate aqueous solution thereto, and then sufficiently agitates it is known in JP Laid-Open Patent No. 2001-136970 and 1994-047273. However, since the above method requires a process of dispersing the ammonium sulfate aqueous solution in the W/O type emulsion and a process of performing a sufficient agitation using an ultrasonic wave, etc., so that the dispersed ammonium sulfate aqueous solution micelle reacts with the sodium silicates aqueous solution micelle, the preparing process is complicated as well as since the size of the sodium silicates aqueous solution micelle is changed in the agitating process with the ammonium sulfate aqueous solution, it is difficult to uniformly control the silica particle size distribution to be formed.

KR Laid-Open Patent No. 2006-0061494 about the magnetic functional silica coated particles discloses a method for preparing magnetic functional silica coated particles by introducing an amine group or a chloro group on a surface as a method for preparing magnetic functional silica coated particles for separating and purifying nucleic acid, DNA, and RNA. However, the preparing method of the above-mentioned patent has disadvantages in that very expensive tetraethyl orthosilicate (TEOS) is used, the preparing process is complicated, and the particles are non-uniform. Further, KR Registration Patent No. 0541282 discloses a method that modifies the magnetic nanoparticles with silane materials and uses it; however, since the used magnetic nanoparticles themselves are magnetic substances, it has problems, such as biotoxicity, etc.

DISCLOSURE OF INVENTION

Technical Problem

The present invention proposes to solve the problems in the related art. An object of the present invention is to provide a novel preparing method that can simplify a preparing process and uniformly control the size of silica magnetic particles, as compared to a method for preparing silica magnetic particles in the related art.

More specifically, an object of the present invention is to a preparing method that can simplify a preparing process, easily induce various functional groups, make prepared silica magnetic particles in a spherical form, and uniformly control the size of silica magnetic particles, by using an emulsion method and adding fatty acid that can be dissolved in non-polar solvents to induce sol-gel reaction in a method for chemically preparing the silica magnetic particles used for separating biomaterials.

Further, another object of the present invention is to provide a method for preparing magnetic functional silica coated particles that can be effectively used for a reagent for separating or purifying biomaterials or for detecting biomaterials by introducing various functional groups on silica magnetic particles having a spherical form prepared from the preparing method.

Technical Solution

The present invention relates to a method for preparing silica magnetic particles having a spherical form that uses an emulsion method and adds fatty acid that can be dissolved in non-polar solvents to induce sol-gel reaction, silica magnetic particles having a spherical form with a uniform particle size distribution prepared from the same, and a method for separating and purifying biomaterials using the silica magnetic particles having the spherical form.

The present invention provides a method for preparing silica magnetic particles having a spherical form including the following steps.

1) preparing emulsion by adding surfactant, soluble silicates aqueous solution, and magnetic particles to a non-polar solvent and then dispersing it using an ultrasonic wave; and 2) preparing silica magnetic particles by adding fatty acid to the emulsion.

Further, the present invention provides silica magnetic particles having a spherical form, which is prepared according to the above preparing method, containing the magnetic particles therein. The silica magnetic particles having a spherical form prepared according to the preparing method of the present invention are shown in FIG. 1 and FIGS. 4 to 6, it can be confirmed from FIG. 1 and FIGS. 4 to 6 that the size of the prepared silica magnetic particles having a spherical form is 1 to 20 μm, and referring to the particle size analyzing results of FIG. 2, it can be appreciated that the particle size distribution is uniform.

A method for preparing silica magnetic particles further includes additionally the step of introducing a functional group on surfaces of the silica magnetic particles prepared in the step 2), after the step 2). The introduction of the functional group can be made through the bonding reaction with compounds for introducing the functional group on the silica magnetic particles by dispersing the silica magnetic particles having a spherical form prepared in the step 2) in the solvents and contacting it with compounds for introducing the functional group.

Preferably, the functional group is one or more selected from an amine group, a carboxylic acid group (—COOH), an epoxy group, a (C1~C30) alkyl group, a streptavidin group, a biotin group, and an iminodiacetic acid group.

The silica magnetic particles prepared in the step 2) has a hydroxyl group (—OH) group on the surface thereof, such that they can be used for separating the biomaterials, specifically, nucleic acid. According to the concrete embodiment, a method for separating the nucleic acid can be provided by using the silica magnetic particles having a spherical form prepared in the step 2) as a nucleic acid bonding carrier and using a reagent for bonding the silica magnetic particles having a spherical form with the nucleic acid, for example, a chaotropic reagent, etc.

The silica magnetic particles having a spherical form prepared through the step of introducing the functional group can be used for a reagent for widely separating or purifying the biomaterials or for detecting the biomaterials through various functional groups.

Hereinafter, the contents of the present invention will be described in detail.

In the present invention, a method for preparing silica magnetic particles having a spherical form for separating biomaterials includes a first step of preparing emulsion by adding surfactant, soluble silicates aqueous solution, and magnetic particles to a non-polar solvent and then dispersing it using an ultrasonic wave, a second step of preparing silica magnetic particles by adding fatty acid to the emulsion and by forming silica by sol-gel reaction, and a third step of preparing functional silica magnetic particles by adding functional compounds to the silica magnetic particles.

In the present invention, the first step for preparing the silica magnetic particles having a spherical form prepares emulsion by adding surfactant, soluble silicates aqueous solution, and magnetic particles to a non-polar solvent and then dispersing it using an ultrasonic wave. When adding an appropriate amount of soluble silicates aqueous solution and surfactant to the non-polar solvent and processing it using the ultrasonic wave, the micelle is formed by the surfactant. Herein, the prepared micelle, which is inverse emulsion, is a form where an aqueous solution micelle is formed on oil that is the non-polar solvent, that is, W/O type emulsion.

Further, the added magnetic particles exist in the micelle by the ultrasonic wave. The micelle having a spherical form including the soluble silicates aqueous solution reacts with the fatty acid added later to completely prepare the silica having a spherical form. The first step of the preparing method according to the present invention is a step that forms the soluble silicates aqueous solution having a uniform size and disperses the magnetic particles so that the magnetic particles exist in the micelle.

In the preparing method according to the present invention, the non-polar solvent is a solvent that can prepare the W/O type emulsion as a solvent having low solubility to water, specifically, can use a solvent having solubility of 8% or less to water. It is preferable that as the non-polar solvent, cyclohexane, hexane, heptane, octane or mixtures thereof are used; however, it is not limited thereto.

It is preferable that as the materials, which can be used as the surfactant in the preparing method according to the present invention, non-ionic surfactant, cationic surfactant, or anionic surfactant is used, but more preferably, the non-ionic surfactant is used. The surfactant can be used as content of 5 to 30 parts by weight for 100 parts by weight of a non-polar solvent, preferably as content of 10 to 25 parts by weight. When the surfactant exceeds 30 parts by weight, it affects the formation of emulsion so that the silica having a spherical form is not prepared. When the surfactant is less than 5 parts by weight, the number of micelles is too small so that the yield of silica magnetic particles having a spherical form is too low, thereby causing the problem in productivity.

In detail, it is preferable that the non-ionic surfactant is polyoxyethylene decyl ether, polyoxyethylene lauryl ether, polyoxyethylene cetyl ether, polyoxyethylene oleyl ether, polyoxyethylene stearyl ether, polyoxyethylene octyl decyl ether, polyoxyethylene tridecyl ether, polyoxyethylene nonylphenol ether, polyoxyethylene octylphenol ether, polyoxyethylene phenyl ether, polyoxyethylene sorbitan ester, sorbitan monolaurate, sorbitan monopalmitate, sorbitan monosterate, sorbitan trioleate, polyoxyethylene glycol, polyoxyethylene oleyl ester, or mixtures thereof; however, it is not limited thereto. It is preferable that the cationic surfactant is dodecyl ammonium chloride, cetyltrimethylammonium bromide, alkylammonium methosulfate, alkyl dimethyl ammonium chloride, or mixtures thereof; however it is not limited thereto. It is preferable that the anionic surfactant is sodium stearate, sodium laurate, sodium palmitate, potassium stearate, potassium laurate, potassium palmitate, sodium lauryl sulfate, sodium dodecylbenzene sulfonate, or mixtures thereof; however, it is not limited thereto.

In the preparing method according to the present invention, as the soluble silicates aqueous liquid, preferably, sodium silicates aqueous solution, potassium silicates aqueous solution, or lithium silicates aqueous solution is used, but more preferably, the sodium silicates aqueous solution is used; however, it is not limited thereto. It is preferable that the morality M of the soluble silicates aqueous liquid is 0.1 mol/L to 5 mol/L.

When the morality is less than 0.1 mol/L, the reaction speed is too slow, thereby causing the problem in the processes and when the morality is too high exceeding 5 mol/L, the reaction speed is too rapid, thereby causing a problem in that silica having a uniform spherical form is not formed.

Preferably, the soluble silicates aqueous solution is used as content of 1 to 20 parts by weight for 100 parts by weight of a non-polar solvent, more preferably as content of 1 to 10 parts by weight. When the soluble silicates aqueous solution exceeds 20 parts by weight, the micelle is too large in the emulsion so that the silica magnetic particles are too largely prepared. When the soluble silicates aqueous solution is less than 1 parts by weight, the micelle of the surfactant is not formed in the emulsion, thereby causing a problem in that the silica magnetic particles having a spherical form is not prepared.

In the preparing method according to the present invention, it is preferable that the material, which can be used as the magnetic particles is one or more selected from iron oxide (hematite, maghemite; $Fe_2O_3$, magnetite; $Fe_3O_4$), ferrite, iron, cobalt, manganese, chromium, nickel, zinc, or mixtures thereof; however, it is not limited thereto. It is most preferable that iron oxide (magnetite) having a size of 100 to 300 nm is used. The magnetic iron oxide particles, which are directly prepared or sold, can be used. The method for preparing magnetic iron oxide particles can prepare iron oxide by preparing magnetic iron particles while generating carbon monoxide by pyrolysis at the time of instantly injecting carbonyl iron in a high-temperature solvent and then oxidizing the prepared magnetic iron particles. As another preparing method, a method for preparing iron oxide by adding ammonia water to a mixing solution of $FeCl_2$ and $FeCl_3$ is widely known.

The magnetic particles can be used as content of 0.01 to 1.0 parts by weight for 100 parts by weight of a non-polar solvent, preferably as content of 0.01 to 0.5 parts by weight. When the magnetic particles exceed 1.0 parts by weight, it exists out of the micelle of the emulsion solution, thereby causing a problem in that silica having a spherical form can not be prepared.

When the magnetic particles are less than 0.01 parts by weight, the number of magnetic substances included in the silica particles is too small, thereby causing a problem in that magnetism for magnetic force is reduced.

In the preparing method according to the present invention, the second step prepares the silica magnetic particles having a spherical form by adding fatty acid that can be dissolved in the non-polar solvent while agitating the emulsion solution prepared in the first step and performing the reaction for forming the silica of the micelle. The fatty acid is directly added to the emulsion or the fatty acid solution, which is dissolved in the non-polar solvent, can be added thereto. It is preferable that a time to add the fatty acid or the fatty acid solution is 10 to 30 minutes and it is advantageous that the agitation is performed at speed as quickly as possible so as to improve the reaction speed for forming the silica. However, when the agitation speed is too quick, since the uniformity of the size of the produced silica magnetic particles can be degraded, it is preferable that the agitation speed is in the range of about 50 to 2000 rpm.

If the fatty acid can be dissolved in the non-polar solution and has acidity, any fatty acid can be used. Further, all of a natural fatty acid and a synthesized fatty acid can be used. Specifically, the fatty acid may include compounds according to the following Formula 1 or mixtures thereof, for example.

R—COOH [Formula 1]

(In the above Formula 1, R is selected from straight or branched alkyl group of C8~C20 and the alkyl group can include a double bond of 1 or more or a triple bond of 1 or more within a carbon chain and can be further substituted with a hydroxy group).

An example of the fatty acid usable in the preparing method according to the present invention may include myristic acid, palmitic acid, lauric acid, stearic acid, linoleic acid, linolenic acid, ricinoleic acid, oleic acid, or mixtures thereof. The fatty acid can be used as content of 0.1 to 10 parts by weight for 100 parts by weight of a non-polar solvent, preferably as content of 1 to 5 parts by weight. When the fatty acid exceeds 10 parts by weight, it affects the formation of emulsion micelle, thereby causing a problem in that the silica having a spherical form is not prepared. When the fatty acid is less than 0.1 parts by weight, there is a problem in that the reaction for synthesizing the silica particles is not completely progressed in the emulsion solution.

Further, the preparing method according to the present invention may further include filtering, washing, and drying after the second step. The filtering uses a microfilter paper. The washing is repetitively performed several times using ethanol and ultra pure water. The drying is performed on the prepared silica magnetic particles having a spherical form at a temperature of 100 to 300° C., preferably 120° C. to 200° C. for 2 hours or more in a drying apparatus.

As an example according to the present invention, photographs of a scanning electron microscope for the prepared silica magnetic particles having a spherical form are shown FIG. 1 and FIGS. 4 to 6 and the particle size analyzing results are shown in FIG. 2. Further, referring to FIG. 1, FIG. 2, and FIGS. 4 to 6, in the preparing method according to the present invention, it can be confirmed that the form of the silica magnetic particles prepared by subjecting to the step 2) is a spherical form and the size of the particles is uniformly prepared in the range of 1 to 20 μm. Further, referring to zeta potential analyzing results of FIG. 3, it can be confirmed that there is a hydroxy group (—OH) on the surfaces of the silica magnetic particles having a spherical form. In other words, when the zeta potential is measured, it indicates a negative value due to the hydroxy group on the surface, wherein the value is in the range of −30 mV to −60 mV as shown in FIG. 3.

On the other hand, as a comparative example, when the silica magnetic particles are prepared using ammonium sulfate aqueous solution instead of the fatty acid, since the size of particles are non-uniform as shown in FIG. 7, it is confirmed that the reproducibility is degraded due to the repetition of the preparing process such that it is difficult to uniformly control the size of particles.

In the preparing method according to the present invention, the step 3) is a step that prepares the functional silica magnetic particles having a spherical form where the silica magnetic particles having a spherical form prepared in the step 2) contact compounds for introducing various functional groups so as to introduce the functional groups. The step 3) can be performed by dispersing the silica magnetic particles having a spherical form prepared in the step 2) in a solvent and then contacting them with the compounds for introducing the functional groups and performing the reaction that bonds the compounds for introducing the functional groups on the surfaces of the silica magnetic particles. Since the hydroxy group (—OH) is formed on the surfaces of the silica magnetic particles having a spherical form prepared in the step 2), the bonding reaction with the compounds for introducing various functional groups can be made. The solvent is not limited in the reaction of the step 3) and water, hydrocarbon solvent, halogenated hydrocarbon solvent, etc. can be used alone or in combinations thereof.

In the present invention, as a kind of the functional group, there is one or more selected from an amine group, a carboxylic acid group, an epoxy group, a (C1~C30) alkyl group, a streptavidin group, a biotin group, and an iminodiacetic acid; however, it is not necessarily limited thereto.

In the preparing method according to the present invention, compounds for introducing an amine group can use silane compounds having an alkyl group where at least one of amine groups (—NH$_2$, —NH—,

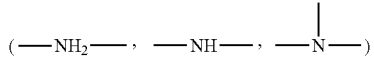

is substituted. As the silane compounds, aminopropyldiisopropylethoxysilane, aminopropyltrimethoxysilane, aminopropyltriethoxysilane, aminopropylmethyldiethoxysilane, aminophenyltrimethoxysilane, phenylaminopropyltrimethoxysilane, aminoethylaminopropyltrimethoxysilane, aminoethylaminopropyltriethoxysilane, aminoethylaminopropylmethyldimethoxysilane, aminoethylaminoisobutylmethyldimethoxysilane, trimethoxysilylpropyldiethylenetriamine, or mixtures thereof can be used; however, it is not necessarily limited thereto.

In the preparing method according to the present invention, it is preferable that the compounds for introducing carboxylic acid is trimethoxysilylpropylethylenediamine triacetic acid; however, it is not necessarily limited thereto. The carboxylic acid can be introduced by reacting dicarboxylic acid anhydride such as succinic anhydride, etc., with the silica magnetic particles into which the amine group is introduced.

In the preparing method according to the present invention, as the compounds for introducing an epoxy group, there are silane compounds having a glycidoxy group or an epoxy group. Specifically, glycidoxypropyltrimethoxysilane, glycidoxypropyltriethoxysilane, glycidoxypropylmethyldimethoxysilane, glycidoxypropylmethyldiethoxysilane, glycidoxypropyldimethylmethoxysilane, glycidoxypropyldimethylethoxysilane, epoxycyclohexylethyltrimethoxysilane, or mixtures thereof can be used; however, it is not necessarily limited thereto.

In the preparing method according to the present invention, the compounds for introducing a (C1~C30) alkyl group can use silane compounds having the (C1~C30) alkyl group. Specifically, trimethoxy (C1~C30) alkylsilane, triethoxy (C1~C30) alkylsilane, or mixtures thereof can be used. It is preferable that as the compounds corresponding thereto, trimethoxyoctadecylsilane, triethoxyoctadecylsilane, or mixtures thereof are used; however, it is not necessarily limited thereto.

In the preparing method according to the present invention, the streptavidin group can be introduced by reacting streptavidin with the silica magnetic particles into which the amine group is introduced; however, it is not limited thereto.

In the preparing method according to the present invention, the biotin group can be introduced by reacting biotin with the silica magnetic particles into which the amine group is introduced; however, it is not limited thereto.

In the preparing method according to the present invention, the iminodiacetic acid group can be introduced by reacting iminodiacetonitrile with the silica magnetic particles into which the epoxy group is introduced; however, it is not limited thereto.

In the functional silica magnetic particles into which the functional group prepared according to the preparing method of the present invention is introduced, magnetic particles having a size of several tens to several hundreds nanometer are enclosed by silica and the functional group layer inducing various functional groups are formed on the silica surfaces. In the case where the functional group is amine groups (—NH$_2$, —NH—,

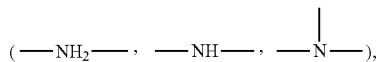

when the zeta potential is measured, it indicates a positive value. When the amine group according to the seventh embodiment is introduced, the value indicates values of +20 mV to +50 mV as shown in FIG. 8. In the case of the functional silica magnetic particles into which carboxylic acid is introduced, when the zeta potential is measured, it indicates a negative value due to a carboxylic acid group (COOH), that is, values of −30 mV to −60 mV. In the case of the functional silica magnetic particles into which the epoxy group or the (C1~C30) alkyl group is introduced, since the functional group does not have potential, the potential does not appear. In the case of the functional silica magnetic particles into which a streptavidin group is introduced, when the zeta potential is measured, it indicates a negative value due to the streptavidin, that is, indicates values of −30 mV to −60 mV.

In the case of the functional silica magnetic particles into which the biotin group is introduced, since the biotin does not have potential, the potential does not appear. In the case of the functional silica magnetic particles into which the iminodiacetic acid is introduced, when the zeta potential is measured, it indicates a negative value due to two carboxylic acid groups (COOH), that is, values of −30 mV to −60 mV.

The silica magnetic particles having a spherical form prepared according to the preparing method according to the present invention can be used for separating the biomaterials in various forms.

Specifically, the method for separating the biomaterials according to the present invention includes the following preparing steps:

forming complexes of silica magnetic particles having a spherical form and biomaterials by inducing the bonding of the silica magnetic particles having a spherical form and the biomaterials;

separating the complexes using external magnetic field; and obtaining the biomaterials from the separated complexes.

As the biomaterials, there are plasmid DNA, genomic DNA, cDNA, PCR DNA (polymerase chain reaction DNA), RNA, siRNA, ribozymes, aptamers, oligonucleotide, DNA primers, protein, peptide, polypeptide, amino acid, recombinant protein, antibody, lipids, or cells, and the like; however, it is not necessarily limited thereto.

Generally, in order for the magnetic particles to be used for separating the nucleic acid, the magnetic particles are coated with silica.

The method for separating the nucleic acid using the silica separates the nucleic acid using chaotropic reagent, which is a widely known method (R. Boom et al., J. Clin. Microbiol., Vol 28(3), p 495-503 (1990)). If the magnetic particles are coated with silica, they are bonded with the nucleic acid using the chaotropic reagent and the silica magnetic particles are separated using external magnetic force, thereby separating the nucleic acid.

The silica magnetic particles having a spherical form prepared by the preparing method according to the present invention can be used for separating the nucleic acid in various forms. As the nucleic acid, there are plasmid DNA, genomic DNA, cDNA, PCR DNA (polymerase chain reaction DNA), RNA, siRNA, ribozymes, aptamers, oligonucleotide, DNA primers, and the like.

The method for separating and purifying the nucleic acid using the silica magnetic particles having a spherical form according to the present invention is as follows. The first step bonds the nucleic acid to the silica magnetic particles by mixing the silica magnetic particles having a spherical form according to the present invention with samples including the nucleic acid to be separated. At this time, a binding buffer can be used. An example of the binding buffer may include the chaotropic reagent. As the chaotropic reagent, there are guanidine salt, urea, chloride, iodide, perchlorate, (iso)thiocyanate, and the like. As the concrete compound, there are sodium perchlorate, guanidine hydrochloride, guanidine isothiocyanate, potassium iodide, potassium thiocyanate, sodium chloride, sodium isothiocyanate, magnesium chloride, sodium iodide, and the like; however, it is not limited thereto. It is preferable that the chaotropic reagent is used at a concentration of 1 to 8 M (mol/L).

The second step of separating the nucleic acid, which is a step that separates the silica magnetic particles to which the nucleic acid is bonded, collects the silica magnetic particles to which the nucleic acid is bonded in a wall surface of a container by external magnetic force and separates and washes the remaining materials that are not bonded.

The third step, which is a step that removes the external magnetic force and separates the nucleic acid from the silica magnetic particles to which the nucleic acid is bonded, separates the nucleic acid to which the silica magnetic particles are bonded by using an elusion buffer (tris-(hydroxymethyl) amino methane buffer).

Advantageous Effects

The silica magnetic particles having a spherical form prepared according to the present invention includes the magnetic particles, has an advantage in that the particle size distribution of silica having the functional group on the surface is uniform and the particle is a spherical form, and can be used as the reagent for separating the biomaterials and for detecting the biomaterials.

BRIEF DESCRIPTION OF DRAWINGS

The above and other objects, features and advantages of the present invention will become apparent from the following description of preferred embodiments given in conjunction with the accompanying drawings, in which:

FIG. 7 FIG. 4 is photographs of a scanning electron microscope (SEM) for silica magnetic particles having a spherical form prepared according to Comparative Example 1.

BEST MODE FOR CARRYING OUT THE INVENTION

Hereinafter, the present invention will be described in detail with reference to examples. However, the following examples illustrate the present invention, by way of example only and the contents of the present invention are not limited to the following examples.

Example 1

Preparing of Silica Magnetic Particles Having a Spherical Form Using Myristic Acid 400 ml of cyclohexane is put in a 2 L flask and 48 ml of polyoxyethylene nonylphenol ether (Dongnam Chem., Korea, MONOPOL NP 1018, number average molecule weight ($M_n$): 585) that is surfactant and 16 mL of sodium silicate aqueous solution (1.5M concentration) are put therein. Thereafter, it is dispersed for 30 minutes using an ultrasonic wave. 0.4 g of iron oxide magnetic particles (magnetite) (SEAHAN, Korea, SMT-02H, average particle size: 300 nm) is put in the solution and dispersed for 30 minutes using an ultrasonic wave. 5.5 g of myristic acid is dissolved in 40 ml of cyclohexane to prepare myristic acid solution and then, the myristic acid solution is dropped for 30 minutes while agitating emulsion solution. After the dropping, the reaction is completely performed by agitating it at 300 rpm under room temperature for 2 hours to obtain silica magnetic particles.

After the reaction completes, products in a reactor are separated by a filter and washed twice using ethanol and ultra pure water. The obtained silica magnetic particles are put in a drier and dried at 160° C. for 2 hours.

Figure 1:
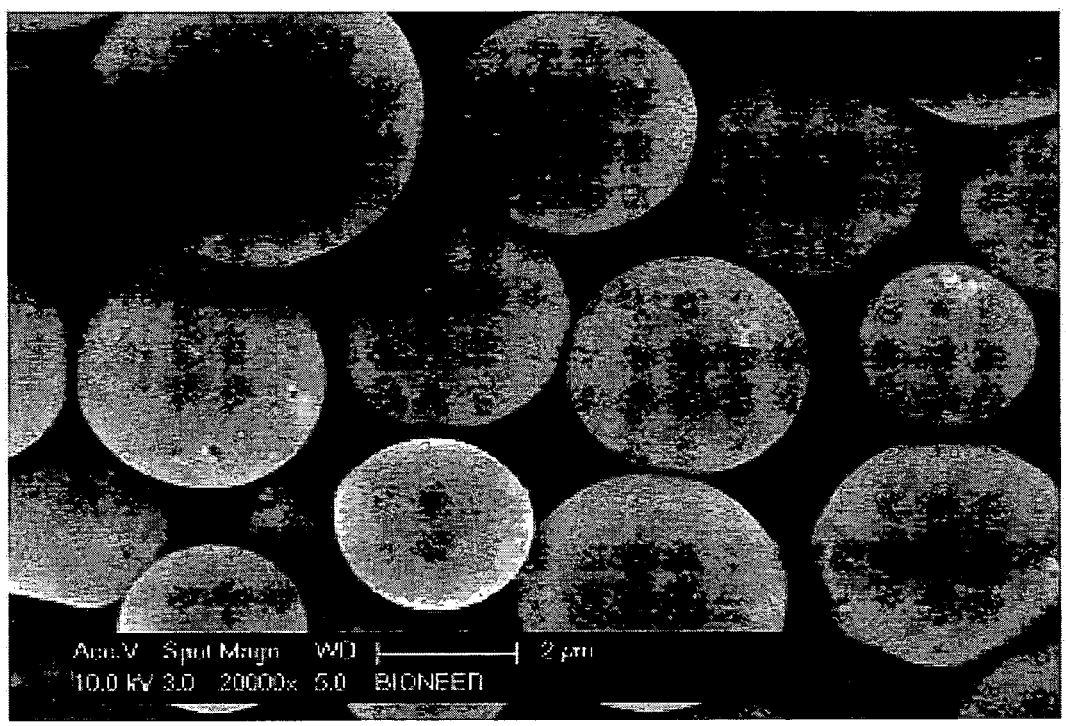
FIG. 1 is photographs of a scanning electron microscope (SEM) for silica magnetic particles having a spherical form prepared according to Example 1.
Figure 2:
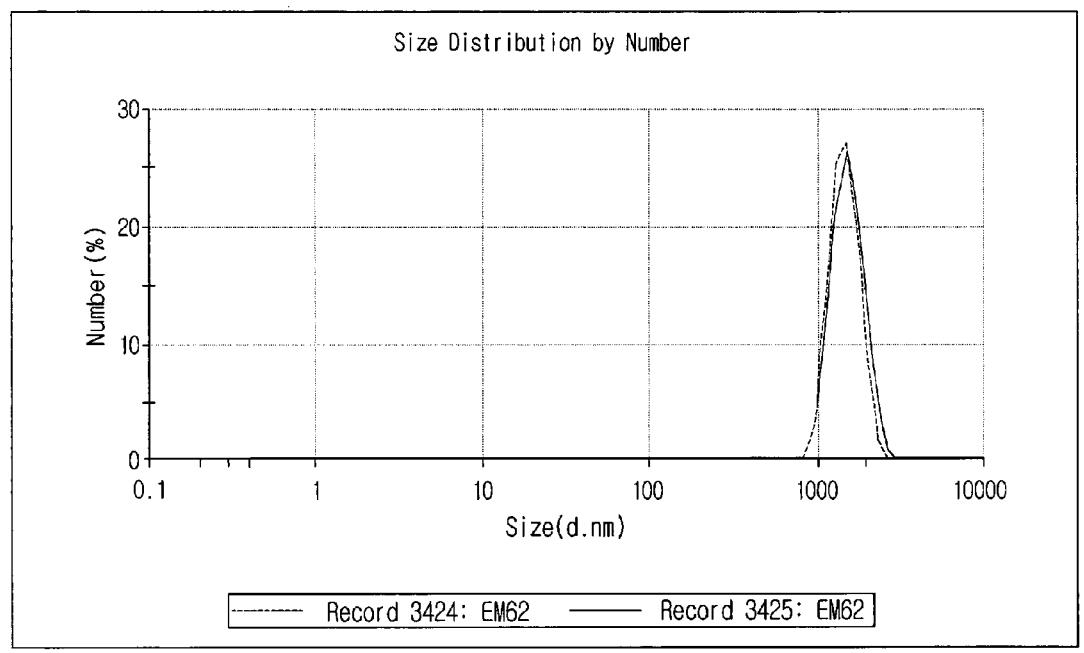
FIG. 2 is particle size analyzing results of the silica magnetic particles having a spherical form prepared according to Example 1.
Figure 3:
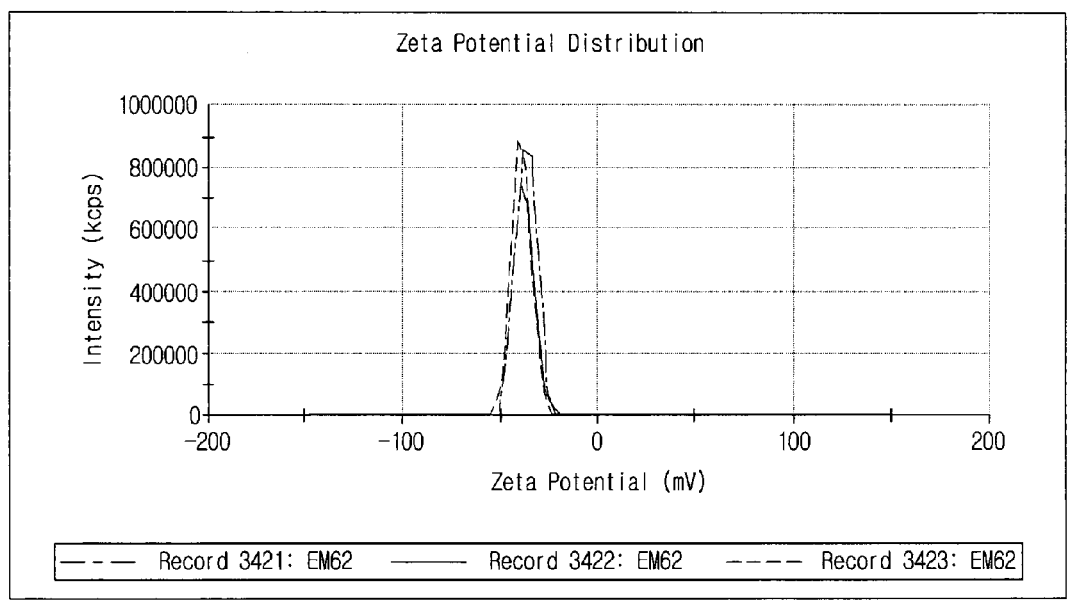
FIG. 3 is zeta potential analyzing results of the silica magnetic particles having a spherical form prepared according to Example 1.

Analysis results of a scanning electron microscope (SEM) for the prepared silica magnetic particles having a spherical form are shown in FIG. 1. It can be confirmed from FIG. 2 that the size of the silica magnetic particles having a spherical form prepared in example 1 is 1.56 μm in average. Further, it can be confirmed that the form thereof is a spherical form and it can be observed that the iron oxide magnetic particles are included inside the silica. The zeta potential of the prepared silica magnetic particles having a spherical form is measured as −39.8 mV as shown in FIG. 3, such that it can be confirmed that a hydroxyl group exists on the silica surface.

Example 2

Preparing of Silica Magnetic Particles Having a Spherical Form Using Palmitic Acid The silica magnetic particles having a spherical form was prepared by being performed under the same conditions as Example 1 except for using palmitic acid solution prepared by dissolving 6 g of palmitic acid in 40 ml of cyclohexane, instead of the myristic acid solution.

The zeta potential of the prepared silica magnetic particles is measured as −33.3 mV, such that it can be confirmed that the hydroxyl group exists on the silica surface.

Example 3

Preparing of Silica Magnetic Particles Having a Spherical Form Using Stearic Acid The silica magnetic particles having a spherical form was prepared by being performed under the same conditions as Example 1 except for using stearic acid solution prepared by dissolving 6.8 g of stearic acid in 40 ml of cyclohexane, instead of the myristic acid solution.

The zeta potential of the prepared silica magnetic particles is measured as −47.0 mV, such that it can be confirmed that the hydroxyl group exists on the silica surface.

Example 4

Preparing of Silica Magnetic Particles Having a Spherical Form Using Lauric Acid The silica magnetic particles having a spherical form was prepared by being performed under the same conditions as Example 1 except for using lauric acid solution prepared by dissolving 4.8 g of lauric acid in 40 ml of cyclohexane, instead of the myristic acid solution.

Figure 4:
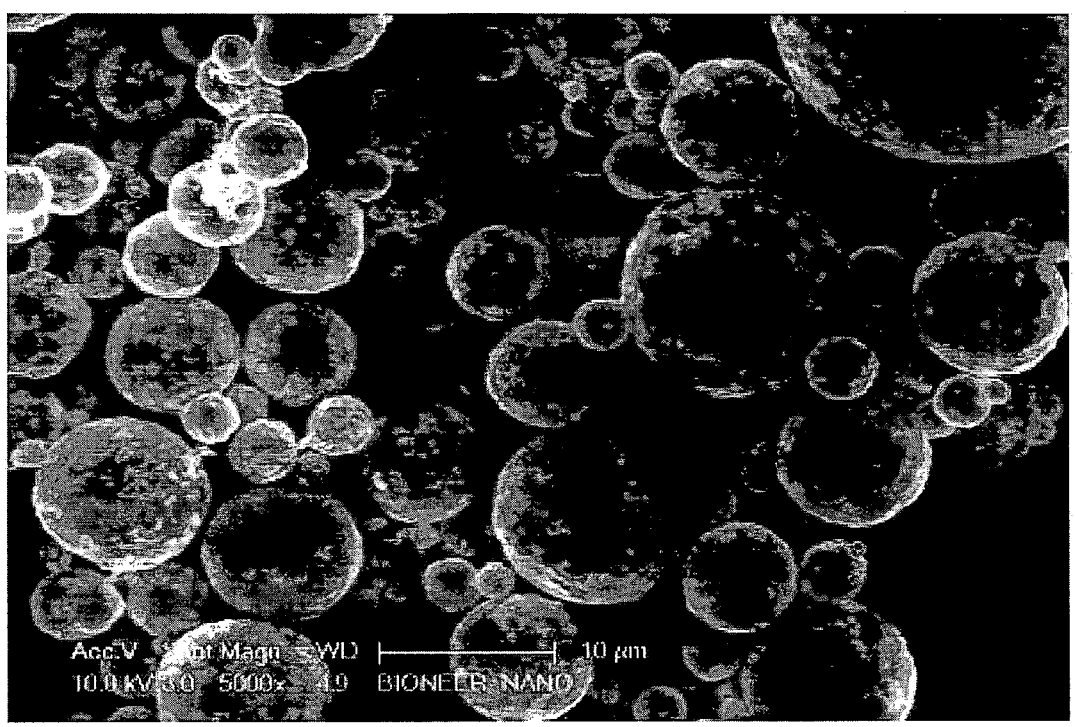
FIG. 4 is photographs of a scanning electron microscope (SEM) for silica magnetic particles having a spherical form prepared according to Example 4.

Analysis results of a scanning electron microscope (SEM) for the prepared silica magnetic particles are shown in FIG. 4. It can be confirmed that the size of the prepared silica magnetic particles having a spherical form is about 1 to 10 μm and the form thereof is a spherical form. Further, it can be observed that the iron oxide magnetic particles (average particle size: 300 nm) are included inside the silica having a spherical form. The zeta potential of the prepared silica magnetic particles is measured as −48.1 mV, such that it can be confirmed that the hydroxyl group exists on the silica surface.

Example 5

Preparing of Silica Magnetic Particles Having a Spherical Form Using Oleic Acid

The silica magnetic particles having a spherical form was prepared by being performed under the same conditions as Example 1 except for using oleic acid solution prepared by dissolving 6.8 g oleic acid in 40 ml cyclohexane, instead of the myristic acid solution.

Figure 5:
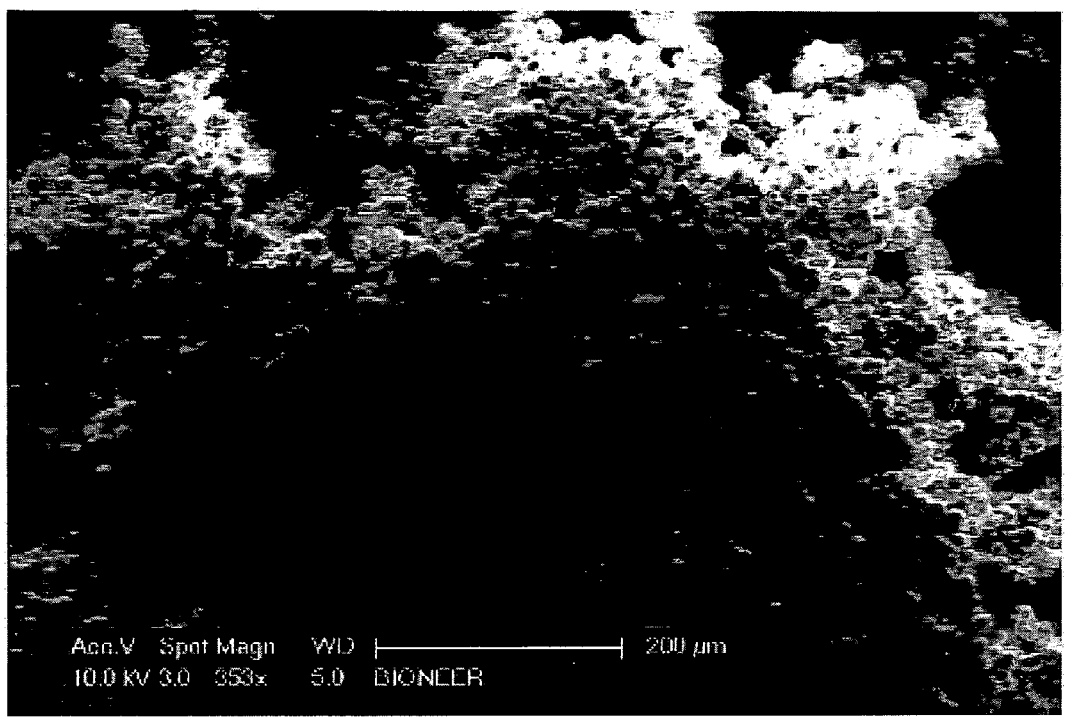
FIG. 5 is photographs of a scanning electron microscope (SEM) for silica magnetic particles having a spherical form prepared according to Example 5.

Analysis results of a scanning electron microscope (SEM) for the prepared silica magnetic particles are shown in FIG. 5. It can be confirmed that the size of the prepared silica magnetic particles having a spherical form is about 1 to 10 μm and the form thereof is a spherical form and uniform. The zeta potential of the prepared silica magnetic particles is measured as −30.1 mV, such that it can be confirmed that the hydroxyl group exists on the silica surface.

Example 6

Preparing of Silica Magnetic Particles Having a Spherical Form Using Myristic Acid (Scale Up)

1200 ml of cyclohexane is put in a 2 L flask and 144 ml of polyoxyethylene nonylphenol ether (Dongnam Chem., Korea, MONOPOL NP 1018, number average molecule weight (Mn): 585) that is surfactant and 48 mL of sodium silicate aqueous solution (1.5M concentration) are put therein.

Thereafter, it is dispersed for 30 minutes using an ultrasonic wave. 0.6 g of iron oxide magnetic particles (magnetite) (SEAHAN, Korea, SMT-02H, average particle size: 300 nm) is put in the solution and dispersed for 30 minutes using an ultrasonic wave. The silica magnetic particles having a spherical form was prepared by being performed under the same conditions as Example 1 except for dissolving 16.5 g of myristic acid in 80 ml of cyclohexane and slowly adding this solution for 30 minutes while agitating it in a reactor having the emulsion solution.

Figure 6:
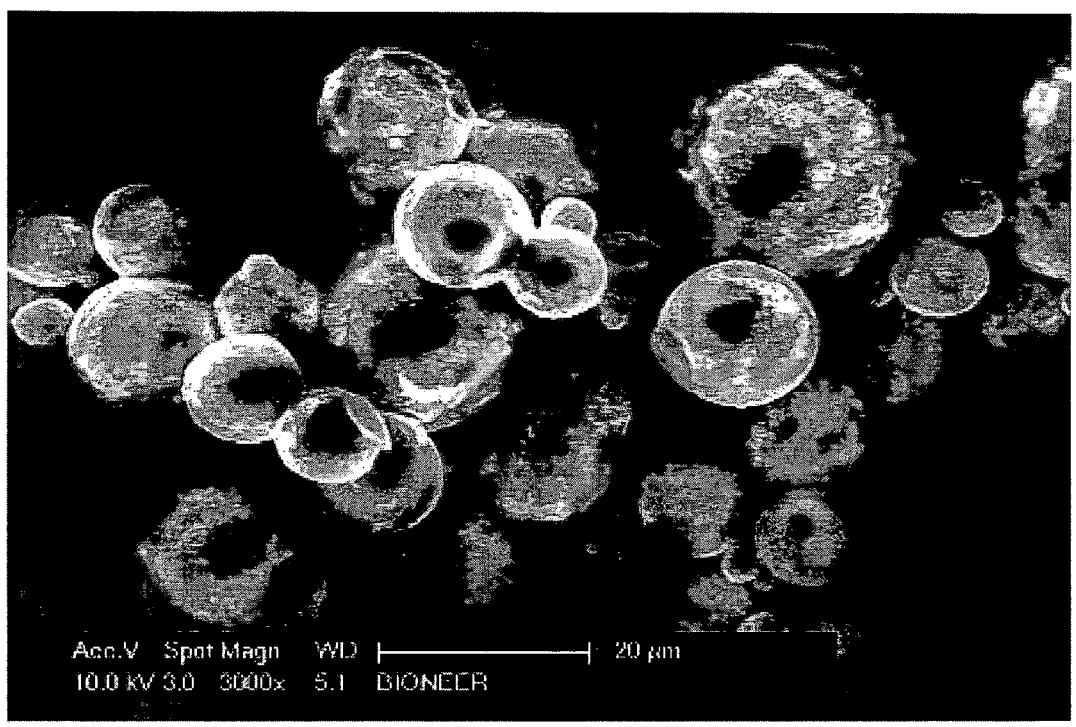
FIG. 6 is photographs of a scanning electron microscope (SEM) for silica magnetic particles having a spherical form prepared according to Example 6.

Analysis results of a scanning electron microscope (SEM) for the prepared silica magnetic particles having a spherical form are shown in FIG. 6. It can be confirmed that the size of the prepared silica magnetic particles is 1 to 20 μm. Further, it can be confirmed that the form thereof is a spherical form and it can be observed that the iron oxide magnetic particles (average particle size: 300 nm) are included inside the silica. The zeta potential of the prepared silica magnetic particles is measured as −33.9 mV, such that it can be confirmed that a hydroxyl group exists on the silica surface.

Comparative Example 1

Preparing of Silica Magnetic Particles Having a Spherical Form Using Ammonium Sulfate Aqueous Solution 800 ml of cyclohexane is put in a 1 L flask and 64 ml of polyoxyethylene nonylphenol ether that is surfactant and 16 mL of sodium silicate aqueous solution (1.5M concentration) are put therein. Thereafter, it is dispersed for 30 minutes using an ultrasonic wave. 0.6 g of iron oxide magnetic particles (magnetite) (SEAHAN, Korea, SMT-02H, average particle size: 300 nm) is put in the solution and dispersed for 30 minutes using an ultrasonic wave.

An agitator is installed and the solution is agitated at room temperature. 16 ml of Ammonium sulfate aqueous solution (1.5M concentration) is added in the reactor while agitating the solution. The reaction is sufficiently performed by agitating it for 2 hours or more at room temperature to obtain the silica magnetic particles. After the reaction completes, products in the reactor are separated by a filter and washed twice using ethanol and ultra pure water. The obtained silica magnetic particles are put in a drier and dried at 120° C. for 2 hours.

Figure 7:
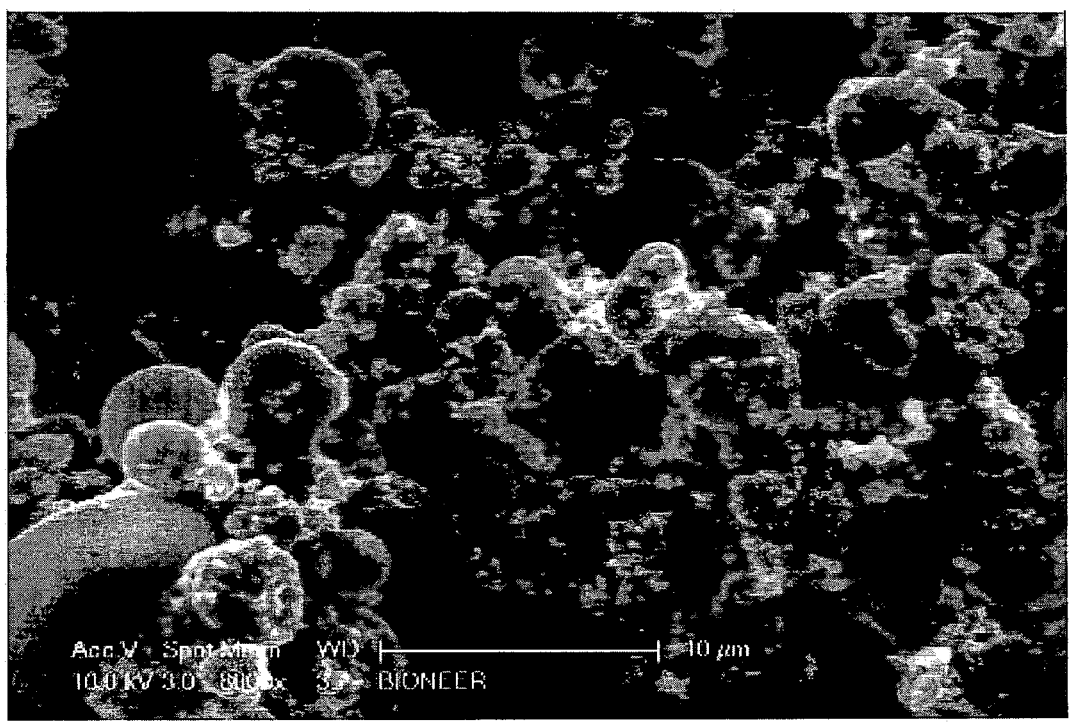

Analysis results of a scanning electron microscope (SEM) for the prepared silica magnetic particles having a spherical form are shown in FIG. 7. It can be confirmed that the size of the prepared silica magnetic particles is about 1 to 10 μm. However, it can be appreciated that the size distribution of the silica magnetic particles is non-uniform as compared to Example 1.

Example 7

Preparing of Silica Magnetic Particles Having a Spherical Form into Which Amine Group is Introduced A 250 mL flask is prepared and the inside of the flask is substituted with nitrogen. 100 ml of octadecene (Aldrich) is put in the flask and the silica magnetic particles having a spherical form of 1 g prepared in Example 1 are added to the reaction flask. Thereafter, it is dispersed for 1 hour using an ultrasonic wave. The silica magnetic particles having a spherical form prepared in Example 1 are dispersed, the flask is mounted on a mantle, and aminopropyltriethoxysilane (Aldrich, USA) of 500 ul is added thereto.

Thereafter, it reacts at 80° C. for 1 hour. If the reaction completes, it is washed three times using methanol and ultra pure water.

Figure 8:
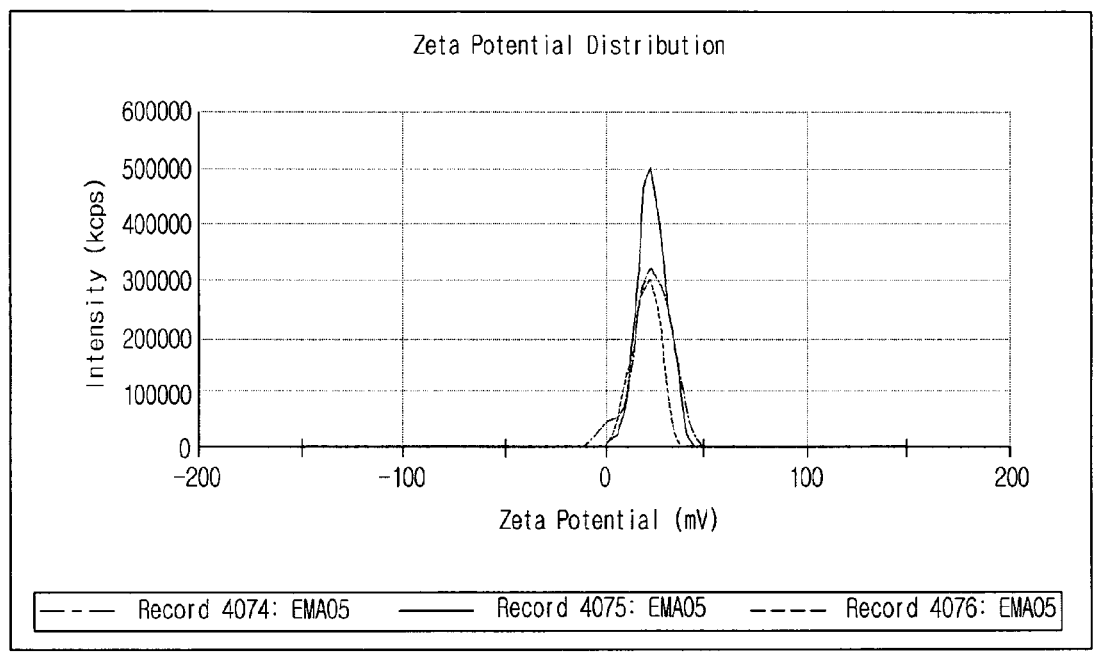
FIG. 8 is zeta potential analyzing results of silica magnetic particles having a spherical form into which an amine group prepared according to Example 7 is introduced.

The zeta potential of the prepared silica magnetic particles having a spherical form is measured as +20.0 mV as shown in FIG. 8, such that it can be confirmed that an amine group exists on the silica surface.

Example 8

Preparing of Silica Magnetic Particles Having a Spherical Form into Which Carboxylic Acid Group is Introduced A 250 mL flask is prepared and the inside of the flask is first substituted with nitrogen. 100 ml of octadecene (Aldrich) is put in the flask and the silica magnetic particles having a spherical form of 1 g introduced with the amine group prepared in Example 7, are added to the reaction flask and dispersed for 1 hour using an ultrasonic wave. And, 4.9 g of succinic anhydride (Aldrich) is added to 20 ml of octadecene and dissolved for 3 hours using an ultrasonic wave. Succinic anhydrie solution is added to the flask in which the silica magnetic particles having a spherical form introduced with the amine group are dispersed and the reaction flask is then mounted on a mantle. Thereafter, it reacts at 80° C. for 1 hour. If the reaction completes, it is washed three times using methanol and ultra pure water.

The zeta potential of the prepared silica magnetic particles having a spherical form into which the prepared carboxylic acid is introduced is measured as −49.9 mV, such that it can be confirmed that the carboxylic acid group exists on the silica surface.

Example 9

Preparing of Silica Magnetic Particles Having a Spherical Form into Which Epoxy Group is Introduced A 250 mL flask is prepared and the inside of the flask is first substituted with nitrogen. 100 ml of octadecene (Aldrich) is put in the flask and the silica magnetic particles having a spherical form of 1 g prepared in Example 1 are added to the reaction flask and dispersed for 1 hour using an ultrasonic wave. After the silica magnetic particles having a spherical form, the flask is mounted on a mantle and 200 ul of 3-glycidoxypropyl trimethoxysilane (Aldrich, USA) is added and reacts at 80 for 1 hour. If the reaction completes, it is washed three times using methanol and ultra pure water.

In the silica magnetic particles having a spherical form into which the prepared epoxy group is introduced, since the epoxy group does not have potential, zeta potential does not appear. In order to confirm this, when measuring the zeta potential by reacting 4 ml polyethyleneimine (PEI; MW=600, Alfa) that reacts with the epoxy group, the zeta potential is measured as +17.3 mV, such that it can be confirmed that the epoxy group exists on the silica surface.

Example 10

Preparing of Silica Magnetic Particles Having a Spherical Form into Which (C18) Alkyl Group is Introduced A 250 mL flask is prepared and the inside of the flask is first substituted with nitrogen. 100 ml of octadecene (Aldrich) is put in the flask and the silica magnetic particles having a spherical form of 1 g prepared in Example 1, are added to the reaction flask and dispersed for 1 hour using an ultrasonic wave. After the silica magnetic particles having a spherical form, the flask is mounted on a mantle and 500 ul of trimethoxyoctadecylsilane (Aldrich) is added and reacts at 80 for 1 hour. If the reaction completes, it is washed three times using methanol and ultra pure water. The silica magnetic particles having a spherical form into which the prepared (C18) alkyl group is introduced does not exhibit zeta potential since the (C18) alkyl group does not have potential.

Example 11

Preparing of Silica Magnetic Particles Having a Spherical Form into Which Streptavidin Group is Introduced A 250 mL flask is prepared and the inside of the flask is first substituted with nitrogen. 100 ml sodium carbonate aqueous solution (100 mM concentration) of pH 11 is put in the flask and the silica magnetic particles having a spherical form of 1 g introduced with the epoxy group prepared in Example 9 is added to the reaction flask. Thereafter, it is dispersed for 1 hour using an ultrasonic wave. After 0.5 mg streptavidin is added to the flask where the silica magnetic particles having a spherical form introduced with the epoxy group is dispersed, the reaction flask is mounted on a mantle and reacts at 60 for 1 hour. If the reaction completes, it is washed three times using methanol and ultra pure water. In order to achieve stability, the silica magnetic particles into which the prepared streptavidin group is introduced are dispersed in a phosphate buffered saline.

The zeta potential of the silica magnetic particles having a spherical form into which the prepared streptavidin group is introduced is measured as −42.9 mV, such that it can be confirmed that the streptavidin group exists on the silica surface.

Example 12

Preparing of Silica Magnetic Particles Having a Spherical Form into Which Biotin Group is Introduced A 250 mL flask is prepared and the inside of the flask is first substituted with nitrogen. 50 ml of dichloromethane (Aldrich) is put in the flask and the silica magnetic particles having a spherical form of 1 g introduced with the amine group prepared in Example 7 is added to the reaction flask and dispersed for 1 hour using an ultrasonic wave. And, 1.0 g of biotin (ESUNG CHEMICALS CO., LTD, Korea) is added to 100 ml of dichloromethane to prepare biotin solution. After the biotin solution and 0.5 ml of diisoprpylcarbodiimide (Acros) are added to the flask where the silica magnetic particles having a spherical form is dispersed, the reaction flask is mounted on a mantle and reacts at 60° C. for 2 hours. If the reaction completes, it is washed three times using methanol and ultra pure water. The silica magnetic particles having a spherical form into which the prepared biotin group is introduced does not exhibit zeta potential since the biotin does not have potential.

Example 13

Preparing of Silica Magnetic Particles Having a Spherical Form into Which Iminodiacetic Acid Group is Introduced A 250 mL flask is prepared and the inside of the flask is first substituted with nitrogen. 100 ml sodium carbonate aqueous solution (100 mM concentration) of pH 11 is put in the flask and the silica magnetic particles having a spherical form of 1 g introduced with the epoxy group prepared in Example 9 is added to the reaction flask. Thereafter, it is dispersed for 1 hour using an ultrasonic wave. 0.5 g of iminodiacetonitrile (Aldrich) is added to 10 ml sodium carbonate solution to prepare iminodiacetonitrile solution. After the iminodiacetonitrile (Aldrich) solution is added to the flask where the silica magnetic particles introduced with the epoxy group are dispersed, the reaction flask is mounted on a mantle and reacts at 60 for 1 hour. If the reaction completes, it is washed three times using methanol and ultra pure water.

The zeta potential of the silica magnetic particles having a spherical form into which the prepared iminodiacetic acid group is introduced is measured as −38.3 mV, such that it can be confirmed that the iminodiacetic acid group exists on the silica surface.

Example 14

Separating Nucleic Acid Using Silica Magnetic Particles Having a Spherical Form

In order to analyze separation efficiency of the prepared silica magnetic particles having a spherical form and the nucleic acid, the following experiment is performed.

After the prepared standard plasmid nucleic acid (standard nucleic acid separated from a colon bacillus cell culture media into which pGEM T-easy vector is introduced) of 2 ug is put in a 1.5 ml tube and the silica magnetic particles of Examples 1, 4, 5, and 6, the silica magnetic particles prepared in Comparative Example 1 for the purpose of comparison, Promega products (MagneSil PMPs, Cat. No. MD1360), and QIAGEN products (EZ DNA Blood 350 ul Kit, Cat. No. 951054) are each put therein by 10 mg, 500 ul reaction solution (4M concentration guanidine hydrochloride, 0.8M concentration potassium acetate (Ph 4.2)) is put therein and they are mixed well. They are left at room temperature for 5 minutes so that the silica magnetic particles and the plasmid nucleic acid can be bonded well. The silica magnetic particles are separated from supernatant using a neodymium magnet and the supernatant is completely removed using a micro pipette. 1 ml of washing solution (80% ethanol) is put therein and is mixed well. The silica magnetic particles are separated from supernatant using the magnet and the supernatant is completely removed using the micro pipette. The same washing process is repeated once more. In order to remove the remaining washing solution, it is dried at 60° C. for 5 minutes.

100 µl of ultra pure water is added to the completely dried silica magnetic particles and is mixed well. They are left at room temperature for 5 minutes so that the silica magnetic particles and the plasmid nucleic acid can be eluted well. The silica magnetic particles are separated using the magnet and the supernatant is acquired by the micro pipette and then transported and put in a new 1.5 ml tube. The separation yield of the plasmid nucleic acid is calculated using ultraviolet absorption spectrometer.

The results are listed in the following Table 1.

TABLE 1

| | Seperation yield of nucleic acid using various silica magnetic particles | | | | | | |
|---|---|---|---|---|---|---|---|
| Silica magnetic particles | Example 1 | Example 4 | Example 5 | Example 6 | Comparative Example 1 | Promega | QIAGEN |
| Separation yield | 47% | 53% | 48% | 43% | 37% | 32% | 34% |

As can be appreciated from Table 1, the silica magnetic particles according to Examples of the present invention exhibit excellent separation yield of nucleic acid as compared to Comparative Example and marketed products.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for preparing silica magnetic particles having a spherical form comprising:
   1) preparing emulsion by adding surfactant, soluble silicates aqueous solution, and magnetic particles to a non-polar solvent and then dispersing it using an ultrasonic wave; and
   2) preparing silica magnetic particles by adding fatty acid to the emulsion.

2. The method according to claim 1, wherein the non-polar solvent is one or more selected from cyclohexane, hexane, heptane, and octane.

3. The method according to claim 1, wherein the surfactant is selected from a group consisting of non-ionic surfactant, cationic surfactant, and anionic surfactant.

4. The method according to claim 3, wherein the non-ionic surfactant is selected from a group consisting of polyoxyethylene decyl ether, polyoxyethylene lauryl ether, polyoxyethylene cetyl ether, polyoxyethylene oleyl ether, polyoxyethylene stearyl ether, polyoxyethylene octyl decyl ether, polyoxyethylene tridecyl ether, polyoxyethylene nonylphenol ether, polyoxyethylene octylphenol ether, polyoxyethylene phenyl ether, polyoxyethylene sorbitan ester, sorbitan monolaurate, sorbitan monopalmitate, sorbitan monosterate, sorbitan trioleate, polyoxyethylene glycol, polyoxyethylene oleyl ester, and mixtures thereof;
the cationic surfactant is selected from a group consisting of dodecyl ammonium chloride, cetyltrimethylammonium bromide, alkylammonium methosulfate, alkyl dimethyl ammonium chloride, and mixtures thereof;
the anionic surfactant is selected from a group consisting of sodium stearate, sodium laurate, sodium palmitate, potassium stearate, potassium laurate, potassium palmitate, sodium lauryl sulfate, sodium dodecylbenzene sulfonate, and mixtures thereof.

5. The method according to claim 3, wherein the surfactant is used as content of 5 to 30 parts by weight for 100 parts by weight of a non-polar solvent.

6. The method according to claim 5, wherein the surfactant is the non-ionic surfactant and is used as content of 10 to 25 parts by weight for 100 parts by weight of a non-polar solvent.

7. The method according to claim 6, wherein the surfactant is polyoxyethylene nonylphenol ether.

8. The method according to claim 1, wherein soluble silicates aqueous solution is selected from sodium silicates aqueous solution, potassium silicates aqueous solution, or lithium silicates aqueous solution.

9. The method according to claim 8, wherein the soluble silicates aqueous solution is used as content of 1 to 20 parts by weight for 100 parts by weight of a non-polar solvent.

10. The method according to claim 9, wherein the soluble silicates aqueous solution is the sodium silicates aqueous solution and is used as content of 1 to 10 parts by weight for 100 parts by weight of a non-polar solvent.

11. The method according to claim 8, wherein the concentration of the soluble silicates aqueous solution is 0.1 mol/L to 5 mol/L.

12. The method according to claim 1, wherein the magnetic particles is one or more particles selected from a group consisting of iron oxide, ferrite, iron, cobalt, manganese, chromium, nickel, zinc, and mixtures thereof.

13. The method according to claim 12, wherein the magnetic particles are used as content of 0.01 to 1.0 parts by weight for 100 parts by weight of a non-polar solvent.

14. The method according to claim 13, wherein the magnetic particles are iron oxide particles and are used as content of 0.01 to 0.5 parts by weight for 100 parts by weight of a non-polar solvent.

15. The method according to claim 1, wherein fatty acid is one or more selected from compounds according to the following Formula 1:

(In the above Formula 1, R is selected from straight or branched alkyl group of C8~C20 and the alkyl group includes a double bond of 1 or more or a triple bond of 1 or more within a carbon chain and is further substituted with a hydroxy group).

16. The method according to claim 1, wherein the fatty acid is selected from a group consisting of myristic acid, palmitic acid, lauric acid, stearic acid, linoleic acid, linolenic acid, ricinoleic acid, oleic acid, and mixtures thereof.

17. The method according to claim 1, wherein the fatty acid is used as content of 0.1 to 10 parts by weight for 100 parts by weight of a non-polar solvent.

18. The method according to claim 16, wherein the fatty acid is myristic acid and used as content of 1 to 5 parts by weight for 100 parts by weight of a non-polar solvent.

19. The method according to claim 1, further comprising a step of introducing functional groups on the surfaces of the silica magnetic particles after the step 2.

20. The method according to claim 19, wherein the functional group is one or more selected from an amine group, a carboxylic acid group, an epoxy group, a (C1~C30) alkyl group, a streptavidin group, a biotin group, and an iminodiacetic acid group.

21. The method according to claim 20, wherein the amine group is introduced from aminopropyldiisopropylethoxysilane, aminopropyltrimethoxysilane, aminopropyltriethoxysilane, aminopropylmethyldiethoxysilane, aminophenyltrimethoxysilane, phenylaminopropyltrimethoxysilane, aminoethylaminopropyltrimethoxysilane, aminoethylaminopropyltriethoxysilane, aminoethylaminopropylmethyldimethoxysilane, aminoethylaminoisobutylmethyldimethoxysilane, trimethoxysilylpropyldiethylenetriamine, or mixtures thereof;
the carboxylic acid group is introduced from trimethoxysilylpropylethylenediamine triacetic acid or introduced by introducing the amine group into the silica magnetic particles and then reacting it with succinic anhydride;
the epoxy group is introduced from glycidoxypropyltrimethoxysilane, glycidoxypropyltriethoxysilane, glycidoxypropylmethyldimethoxysilane, glycidoxypropylmethyldiethoxysilane, glycidoxypropyldimethylmethoxysilane, glycidoxypropyldimethylethoxysilane, epoxycyclohexylethyltrimethoxysilane, or mixtures thereof;
the (C1~C30) alkyl group is introduced from trimethoxy (C1~C30)alkylsilane, triethoxy (C1~C30)alkylsilane (triethoxyoctadecylsilane), or mixtures thereof;
the streptavidin group is introuduced by introducing the amine group into the silica magnetic particles and then reacting it with streptavidin;
the biotin group is introduced by introducing the amine group into the silica magnetic particles and then reacting it with biotin;
the iminodiacetic acid group is introduced by introducing the epoxy group into the silica magnetic particles and then reacting it with iminodiacetonitrile.

22. Silica magnetic particles having a spherical form for separating biomaterials prepared from the preparing method of claim 20, in which the silica magnetic particles have functional groups on their surfaces to form complexes of the silica magnetic particles and biomaterials.

23. A method for separating biomaterials, comprising:
preparing emulsion by adding surfactant, soluble silicates aqueous solution, and magnetic particles to a non-polar solvent and then dispersing it using an ultrasonic wave;
preparing silica magnetic particles having a spherical form by adding fatty acid to the emulsion;
forming complexes of the silica magnetic particles having a spherical form and biomaterials by inducing the bonding of the silica magnetic particles having a spherical form and the biomaterials;
separating the complexes using external magnetic field; and
obtaining the biomaterials from the separated complexes.

24. The method for separating biomaterials according to claim 23, wherein the biomaterial is nucleic acid.

25. The method for separating biomaterials according to claim 24, wherein the nucleic acid is selected from a group consisting of plasmid DNA, genomic DNA, cDNA, PCR DNA (polymerase chain reaction DNA), RNA, siRNA, ribozymes, aptamers, and oligonucleotide.

* * * * *

UNITED STATES PATENT AND TRADEMARK OFFICE
CERTIFICATE OF CORRECTION

PATENT NO.         : 8,697,020 B2                                                Page 1 of 1
APPLICATION NO. : 12/867413
DATED              : April 15, 2014
INVENTOR(S)        : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 888 days.

Signed and Sealed this
Twenty-ninth Day of September, 2015

Michelle K. Lee
*Director of the United States Patent and Trademark Office*